United States Patent
Xia et al.

(10) Patent No.: US 8,822,441 B2
(45) Date of Patent: Sep. 2, 2014

(54) ECDYSTERONE SYNTHESIS DERIVATIVE, PREPARATION METHOD AND USE THEREOF

(75) Inventors: Yongpeng Xia, Chongqing (CN); Xiaolin Wang, Chongqing (CN); Yong Qin, Chongqing (CN); Zongyin Qiu, Chongqing (CN); Lirong Xu, Chongqing (CN); Min Zhang, Chongqing (CN); Dan Zhang, Chongqing (CN); Bao Ding, Chongqing (CN); Qiu Chen, Chongqing (CN)

(73) Assignee: Chongqing Zen Pharmaceutical Co., Ltd., Chongqing (CN)

( * ) Notice: Subject to any disclaimer, the term of this patent is extended or adjusted under 35 U.S.C. 154(b) by 112 days.

(21) Appl. No.: 13/696,330

(22) PCT Filed: May 6, 2011

(86) PCT No.: PCT/CN2011/073791
§ 371 (c)(1),
(2), (4) Date: Nov. 6, 2012

(87) PCT Pub. No.: WO2011/137759
PCT Pub. Date: Nov. 10, 2011

(65) Prior Publication Data
US 2013/0053586 A1     Feb. 28, 2013

(30) Foreign Application Priority Data
May 7, 2010   (CN) .......................... 2010 1 0168580

(51) Int. Cl.
*A61K 31/58*     (2006.01)
*C07J 51/00*     (2006.01)
*C07J 9/00*      (2006.01)
*C07J 71/00*     (2006.01)

(52) U.S. Cl.
CPC .. *C07J 51/00* (2013.01); *C07J 9/00* (2013.01); *C07J 71/0026* (2013.01)
USPC .......................... 514/172; 552/506

(58) Field of Classification Search
CPC ....................................... C07J 51/00
USPC .......................... 552/506; 514/172
See application file for complete search history.

(56) References Cited

FOREIGN PATENT DOCUMENTS

| CN | 1557324 A | 12/2004 |
|----|-----------|---------|
| JP | 2007181432 | 7/2007 |

OTHER PUBLICATIONS

Zhang, Dan et al. (2011) "Synthesis of a novel phosphate analog of 20-hydroxylecdysone with potent hypoglycemic activity," Journal of Asian Natural Products Research, 13(4):297-303.
R. Yamada and H. Sonobe (2003) "*Purification, Kinetic Characterization, and Molecular Cloning of a Novel Enzyme Ecdysteriod-phosphate Phosphatase*," J. Biol. Chem. 278(29):26365-26373.
P. Kizelsztein et al. (2009) "*20-Hydroxyecdysone decreases weight and hyperglycemia in a diet-induced obesity mice model*," J. Physiol. Endocrinol. Metab. 296:E433-E439.

*Primary Examiner* — Barbara P Badio
(74) *Attorney, Agent, or Firm* — William C. Schrot; AuerbachSchrot LLC

(57) ABSTRACT

This invention discloses a novel compound with the structure of formula I, or pharmaceutically acceptable salts or solvates thereof. In addition, the invention further discloses a method for preparing the compound, a pharmaceutical composition containing the compound, and use thereof in the preparation of a hypoglycemic medicament.

(I)

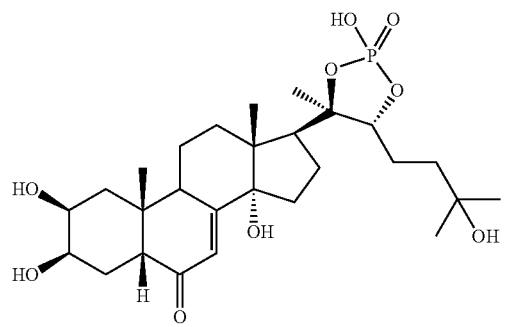

14 Claims, No Drawings

ECDYSTERONE SYNTHESIS DERIVATIVE, PREPARATION METHOD AND USE THEREOF

TECHNICAL FIELD

The invention relates to natural medicine chemistry, and particularly, to a novel ecdysterone synthesis derivative, preparation method and use thereof.

BACKGROUND OF THE RELATED ART

Ecdysterone is a joint name of a kind of natural products that were first discovered in insects. Ecdysterones have molting activity, as well as the effect for promoting cell growth. After 1960s, people found that ecdysterones are also present in plants. Their distribution in plants is higher and wider than that in animals. The ecdysterones are widely present in plants such as Twotoothed Achyranthes Root, Mulberry Leaf, rhaponticum uniflorum and the like. The amounts of ecdysterones in insect body are extremely low. Therefore, currently plant ecdysterones are the main source of commercial ecdysterones. The researches show that ecdysterones possess a variety of pharmacological actions, such as promoting the synthesis of ribonucleic acid and protein, effecting the saccharometabolism, promoting lipid metabolism, immunoloregulation, effecting central nervous system, anti-oxidation, activating blood circulation to dissipate blood stasis and the like.

Chinese Patent CN 1280010A published at Jan. 17, 2001 to Chongren Yang et al. discloses an oral medicament for treating diabetes comprising β-ecdysone and 2-β-ecdysone acetate as the medicinal active ingredients in a weight ratio of 50-95% β-ecdysone to 5-50% 2-β-ecdysone acetate.

Chinese Patent CN 1557324A published at Dec. 29, 2004 to Qiu Chen et al. discloses the use of ecdysterone in preparation of a medicament for treating insulin resistance.

"The effect of ecdysterone on glucose consumption of HepG2 cells" in CHINESE PHARMACOLOGICAL BULLETIN, vol 11, 2005, Qiu Chen et al. discloses that the ecdysterone in a concentration range of $1 \times 10^{-6} \sim 10^{-4}$ mol·L$^{-1}$ increases the glucose consumption of HepG2 cells (by 44%~77%); the effect of ecdysterone on lowering glucose decreases as the increase of glucose concentration in culture solution; and insulin does not obviously effect the action of ecdysterone for lowering glucose. Ecdysterone does not have the action of stimulating insulin secretion of β-TC3 cells, which suggests that ecdysterone can play a non-insulin dependent function of lowering glucose through hepatocyte, but cannot stimulate insulin secretion.

"The effect of ecdysterone on protein expression of insulin receptor in insulin resistant HepG2 cells", SHANDONG MEDICAL JOURNAL, vol 04, 2008, Qiu Chen et al. discloses that $1 \times 10^{-5}$ mol/L of ecdysterone significantly increases the expression of InsR protein in IR HepG2 cells, showing that insulin sensitization by ecdysterone may be associated with the increased expression of InsR protein, an insulin signal transduction molecule.

"The effect of ecdysterone on the protein expression of PI3K, Glut-4 in insulin resistant HepG2 cells", JIANGSU MEDICAL JOURNAL, vol 3, 2009 Chen et al. discloses that $1 \times 10^{-5}$M ecdysterone increases the expression of PI3K and GLUT-4 proteins in insulin resistant HepG2 cells (P<0.05), showing that insulin sensitization by ecdysterone may be associated with the increased expression of PI3K and GLUT-4 proteins which are insulin signal transduction molecules.

"A proteomic study on the insulin resistant HepG2 cell treated by ecdysterone", CHINESE PHARMACOLOGICAL BULLETIN, vol 12, 2009, Min Song et al. discloses the effect of ecdysterone on glucose consumption in insulin resistant model cells, showing that the targets for insulin sensitization by ecdysterone relate to a variety of insulin resistance related proteins and kinases.

In addition, ecdybase.org discloses separated phosphate derivatives of ecdysterone as follows:

1. 26-hydroxyecdysterone-2-phosphate (THOMPSON, J. A. et al., (1987) Arch. Insect Biochem. Physiol. 4, 183-190);
2. 26-hydroxyecdysterone-26-phosphate (THOMPSON, M. J. et al., (1985) Arch. Insect Biochem. Physiol. 2, 227-236);
3. 20-hydroxyecdysterone-22-phosphate (TSOUPRAS, G. et al., (1982) Steroids 40, 551-560);
4. 20-hydroxyecdysterone-3-acetate2-phosphate (ISAAC, R. E. et al., (1984) Biochem. J. 231, 459-464);
5. 20-hydroxyecdysterone-3(2)-phosphate (TSOUPRAS, G. et al., (1983) C. R. Acad. Sci. Paris, Sér. III, 296, 77-80);
6. 20-hydroxyecdysterone-3(2)-acetate-22-phosphate (TSOUPRAS, G. et al., (1983) C. R. Acad. Sci. Paris, Sér. III, 296, 77-80);
7. ecdysterone-3-phosphate (TSOUPRAS, G. et al., (1982) (Thesis, Strasbourg, France));
8. ecdysterone-2-phosphate (ISAAC, R. E. et al., (1984) Biochem. J. 217, 239-243);
9. ecdysterone-2,3-diacetate-22-phosphate (TSOUPRAS, G. et al., (1982) (Thesis, Strasbourg, France));
10. ecdysterone-2-acetate-3-phosphate (ISAAC, R. E. et al., (1984) Biochem. J. 217, 239-243);
11. ecdysterone-3(2)-acetate-22-phosphate (ISAAC, R. E. et al., (1984) Biochem. J. 231, 459-464).

CONTENT OF THE INVENTION

The inventors have unexpectedly prepared a novel compound with a stable structure, good water-solubility and excellent activity in lowering glucose by using 20-hydroxy-β-ecdysterone, a kind of ecdysterone compounds, as a starting material in a large number of ecdysterone derivative researches.

An object of this invention is to provide an ecdysterone derivative.

Another object of this invention is to provide a method for preparing the ecdysterone derivative described above.

Another object of this invention is to provide a pharmaceutical composition comprising the ecdysterone derivative described above.

Another object of this invention is to provide the use of the ecdysterone derivative described above in preparation of hypoglycemic medicament.

Particularly, in the technical solution of this invention, the invention provides a compound with the structure of the following formula I:

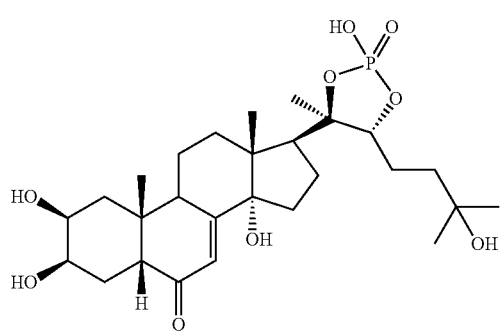

I or pharmaceutically acceptable salts or solvates thereof.

In the technical solution of this invention, the pharmaceutically acceptable salts are selected from metal salts, or organic amine or ammonium salts, wherein the metal salts are selected from alkali metal salts, alkaline earth metal salts; the alkali metal salts are selected from the salts of lithium, sodium, potassium or cesium or the like; the alkaline earth metal salts are selected from the salts of calcium, magnesium or aluminium or the like; the organic amine or ammonium salts are selected from primary amine, secondary amine, tertiary amine, or quaternary ammonium salts of C1-C4 alkyl.

In the technical solution of this invention, the invention provides a sodium salt of compound of formula I, whose structure is the following formula I':

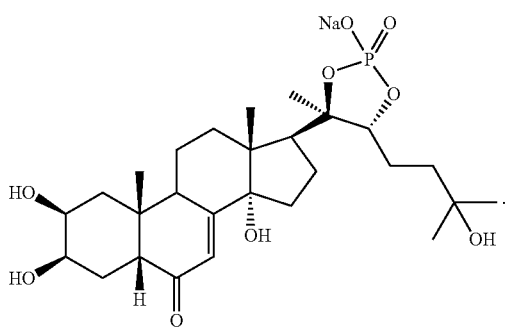

I'

In the technical solution provided by this invention, the solvates are selected from organic solvates or hydrates, wherein the organic solvates are selected from C1-C4 alkanol, such as methanol, ethanol, propanol, isopropanol or butanol or the like; or dimethylformamide; or dimethyl sulfoxide or the like.

In another aspect, the invention provides a method for preparing the compound of formula I as described above, or the pharmaceutically acceptable salts or solvates thereof, comprising the following steps of:

(1) using 20-hydroxy-β-ecdysterone as a starting material to react with phenylboronic acid in the presence of an organic solvent, to yield a compound of formula II:

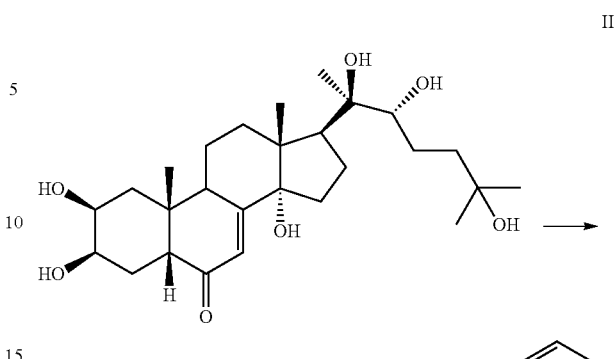

(2) reacting the compound of formula II with a compound of formula III under acidic condition to yield a compound of formula IV; wherein, $R_1$ and $R_2$ in the compounds of formulas III and IV are each independently hydrogen, C1-C4 alkyl or phenyl, $R_X$ and $R_Y$ in the compound of formula III are each independently C1-C4 alkyl, phenyl, or $R_XO$— and $R_YO$—, together with the carbon to which they are attached, form carbonyl, preferably $R_1$, $R_2$, $R_X$ and $R_Y$ in the compound of formula III are simultaneously methyl:

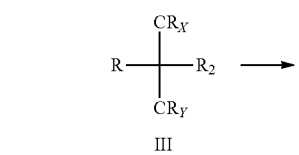

-continued

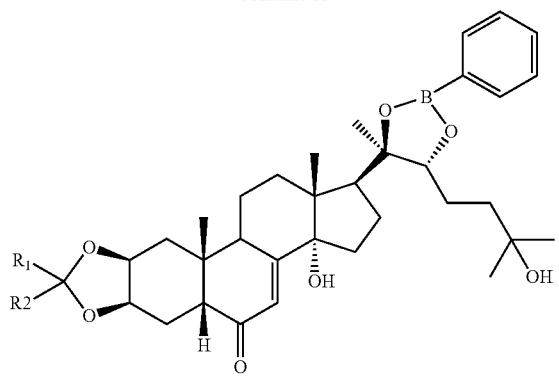

IV (3) reacting the compound of formula IV with a compound of formula V, to yield a compound of formula VI, wherein $R_3$, $R_4$ and $R_5$ in formula V are each independently selected from C1-C4 alkyl, preferably, $R_3$, $R_4$ and $R_5$ are simultaneously methyl or ethyl; X is halogen, and preferably X is chlorine; the definitions of $R_1$, $R_2$, $R_3$, $R_4$ and $R_5$ in formula VI are the same as those in formula IV and formula V:

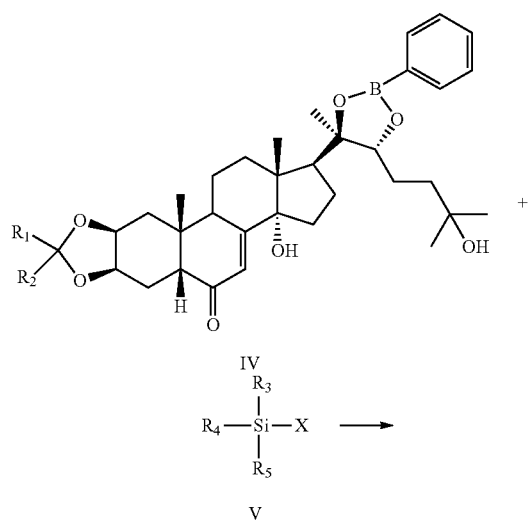

IV

V

VI (4) deprotecting the compound of formula VI in the presence of a base and a peroxide, to yield a compound of formula VII; the definitions of $R_1$, $R_2$, $R_3$, $R_4$ and $R_5$ in formula VII being the same as those in formula IV and formula V:

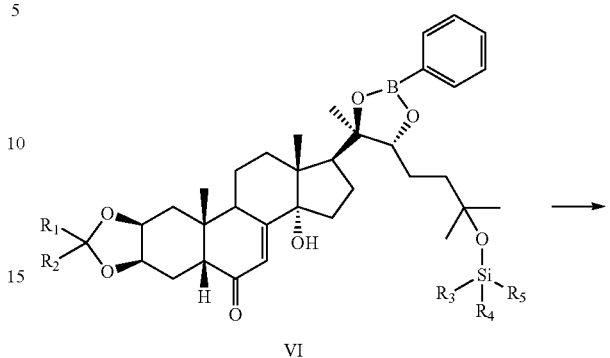

VI

VII (5) reacting the compound of formula VII with $POCl_3$, to yield the compound of formula VIII, the definitions of $R_1$, $R_2$, $R_3$, $R_4$ and $R_5$ in formula VIII being the same as those in formula IV and formula V:

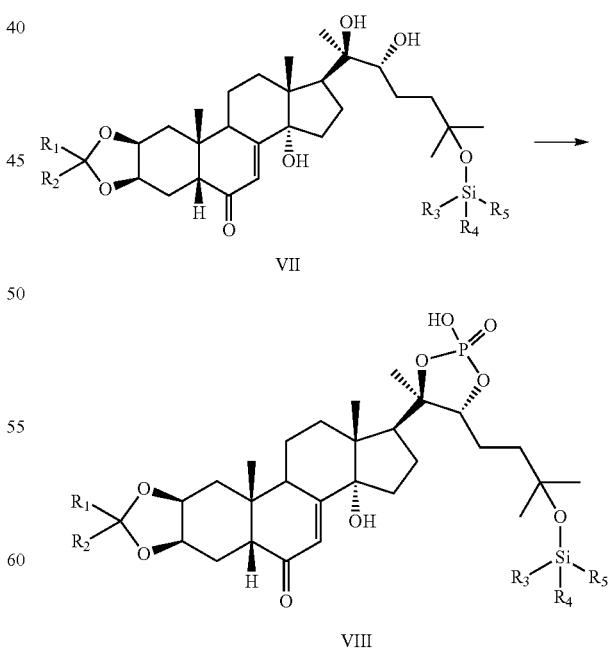

VII

VIII (6) deprotecting the compound of formula VIII under acidic condition, to yield the compound of formula I:

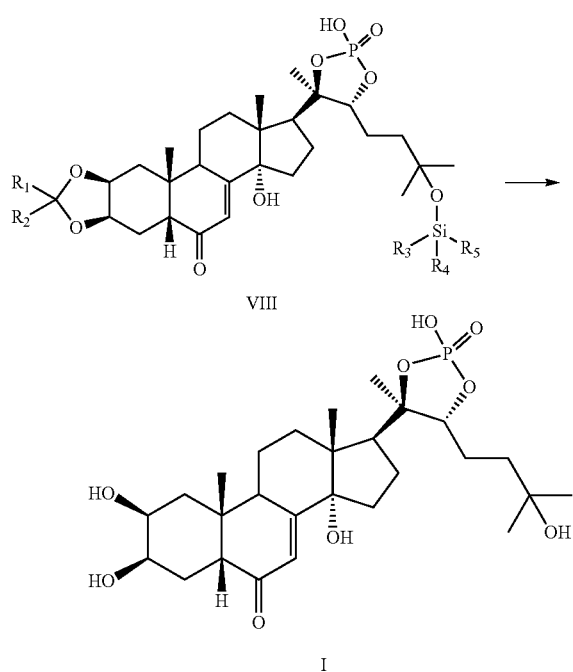

In the preparation method as described above provided by this invention, optionally, after obtaining the compound of formula I in step (6), a conventional salification method in the art is used to yield the salt of the compound of formula I.

In the preparation method as described above provided by this invention, optionally, step (6) is deprotecting the compound of VIII under acidic condition, and then a conventional salification method is used to yield the salt of the compound of formula I. For example, the compound of VIII was deprotected under acidic condition, and then NaHCO$_3$ was added to react, yielding sodium salt of the compound of formula I:

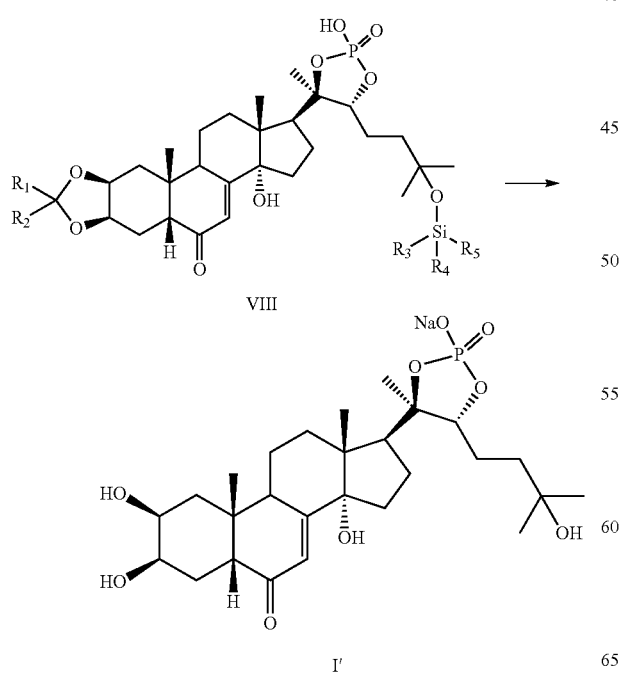

In the preparation method as described above provided by this invention, in the step (1), the organic solvent is selected from dimethylacetamide, dimethylformamide, tetrahydrofuran or dimethyl sulfoxide or the like; the reaction temperature is 0~50° C., and more preferably, the reaction is at room temperature.

In the preparation method as described above provided by this invention, in the step (2), the acidic condition means in the presence of an acidic catalyst. The acidic catalyst is selected from para-toluenesulfonic acid, pyridinium para-toluenesulfonate, or stannous chloride or the like.

In the preparation method as described above provided by this invention, the reaction in the step (3) is carried out in the presence of an organic base and an activator. The organic base is selected from imidazole, N-methylmorpholine, pyridine, or triethylamine or the like. The activator is selected from DMAP (4-dimethylaminopyridine), or dimethylformamide or the like.

In the preparation method as described above provided by this invention, in the step (4), the base is sodium hydroxide, potassium hydroxide, potassium carbonate, sodium carbonate or the like, and the peroxide is hydrogen peroxide.

In the preparation method as described above provided by this invention, the reaction in the step (5) is carried out in the presence of an organic base. The organic base is selected from pyridine, triethylamine, imidazole or the like.

In the preparation method as described above provided by this invention, the acidic condition in the step (6) refers to hydrochloric acid, acetic acid, fluohydric acid, sulfuric acid, para-toluenesulfonic acid or the like.

In the third aspect, the invention provides a pharmaceutical composition comprising the compound of formula I, or the pharmaceutically acceptable salts or solvates thereof, wherein the pharmaceutical composition comprises an effective amount of the compound of formula I, or the pharmaceutically acceptable salts or solvates thereof. The effective amount is, for example, about 0.01 mg to 1000 mg. The pharmaceutical composition provided by the invention further comprises a pharmaceutically acceptable excipient. In addition, the pharmaceutical composition provided by the invention can be formulated into a formulation suitable for oral administration, external administration or injection, such as tablet, solid granula, capsule, injection or lyophilized powder.

In the fourth aspect, the invention provides the use of the compound of formula I as described above, or the pharmaceutically acceptable salts or solvates thereof in preparation of a hypoglycemic medicament. The daily dose is about 0.01 mg to 1000 mg depending on the species, age, gender, administration mode and condition.

The in vitro experiments of glucose consumption in HepG2 cells carried out by using the compound of formula I provided by the invention, shows that the compound possesses significant activity in lowering glucose, and in a concentration range of $2\times10^{-7}$~$2\times10^{-9}$M, can increase the glucose consumption in HepG2 cells by above 500%. Whereas 20-hydroxy-β-ecdysterone in the concentration of $2\times10^{-7}$~$2\times10^{-8}$ M increases the glucose consumption in HepG2 cells by below 15%, and when the concentration is diluted into $2\times10^{-9}$ M, 20-hydroxy-β-ecdysterone has no effect for lowering glucose in HepG2 cells. Therefore, when compared with the activity in lowering glucose of the parent compound 20-hydroxy-β-ecdysterone, the activity in lowering glucose of the compound of formula I is significantly superior to that of 20-hydroxy-β-ecdysterone. The dissolution experiment shows that the solubility in water of the compound of formula I or the sodium salt thereof is 10 fold and 50 fold of that of 20-hydroxy-β-ecdysterone respectively. Moreover, in vivo pharmacological experiment shows that the compound of formula I and the sodium salt thereof possesses the effect for lowering glucose.

Additionally, in the examples, the compound of formula I, rather than ecdysterone 20 or 22-monophosphate, was obtained finally, which further demonstrates that the compound of formula I forms a five-member phosphate lactone with a stable structure

PREFERRED EMBODIMENTS OF THE INVENTION

The embodiments of the invention will be further illustrated with reference to the following examples. For a skilled person in the art, modifications made based on the prior art with the teachings of the invention are still within the protection scope claimed by the invention.

The synthesis route of the compound of formula I or the sodium salt thereof

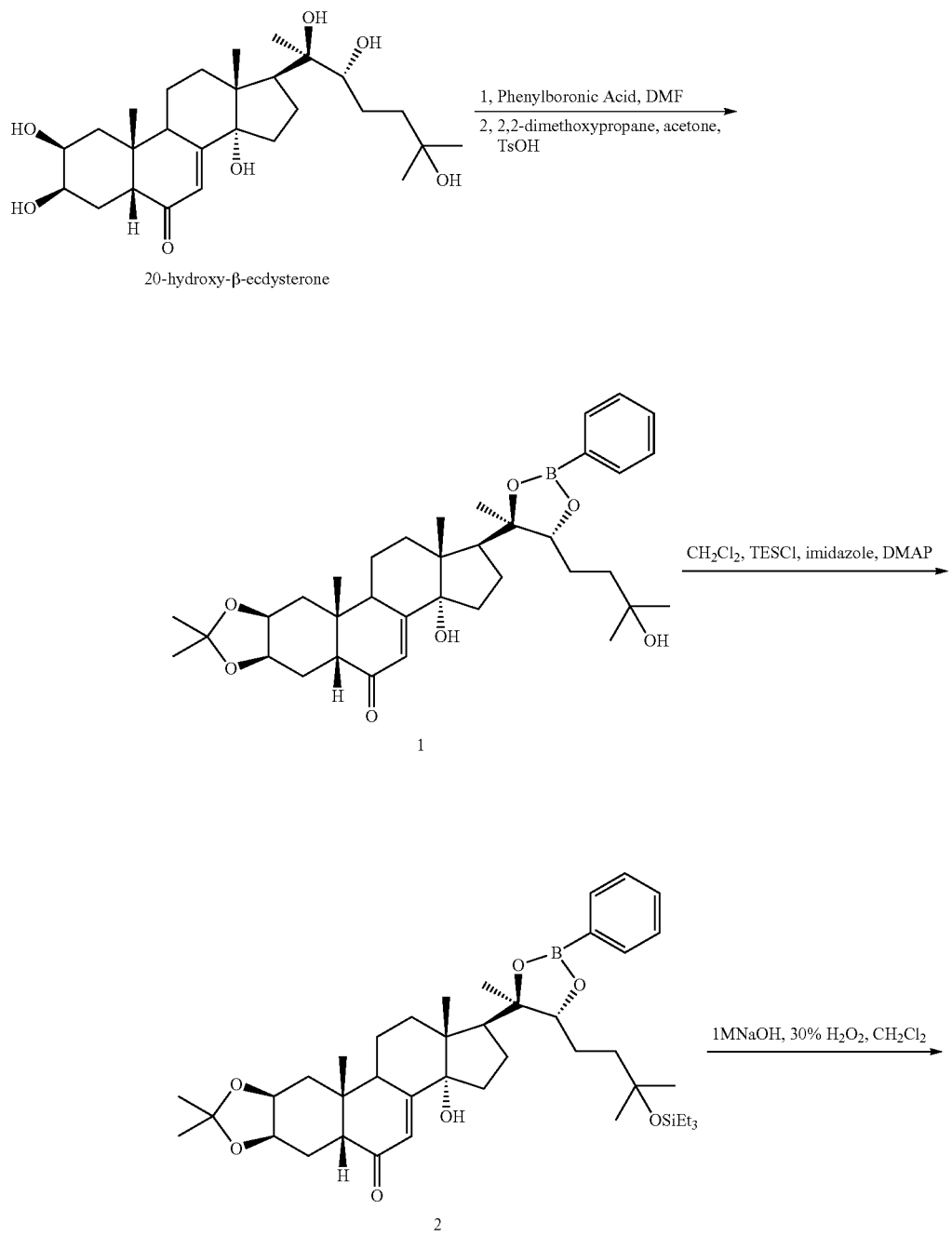

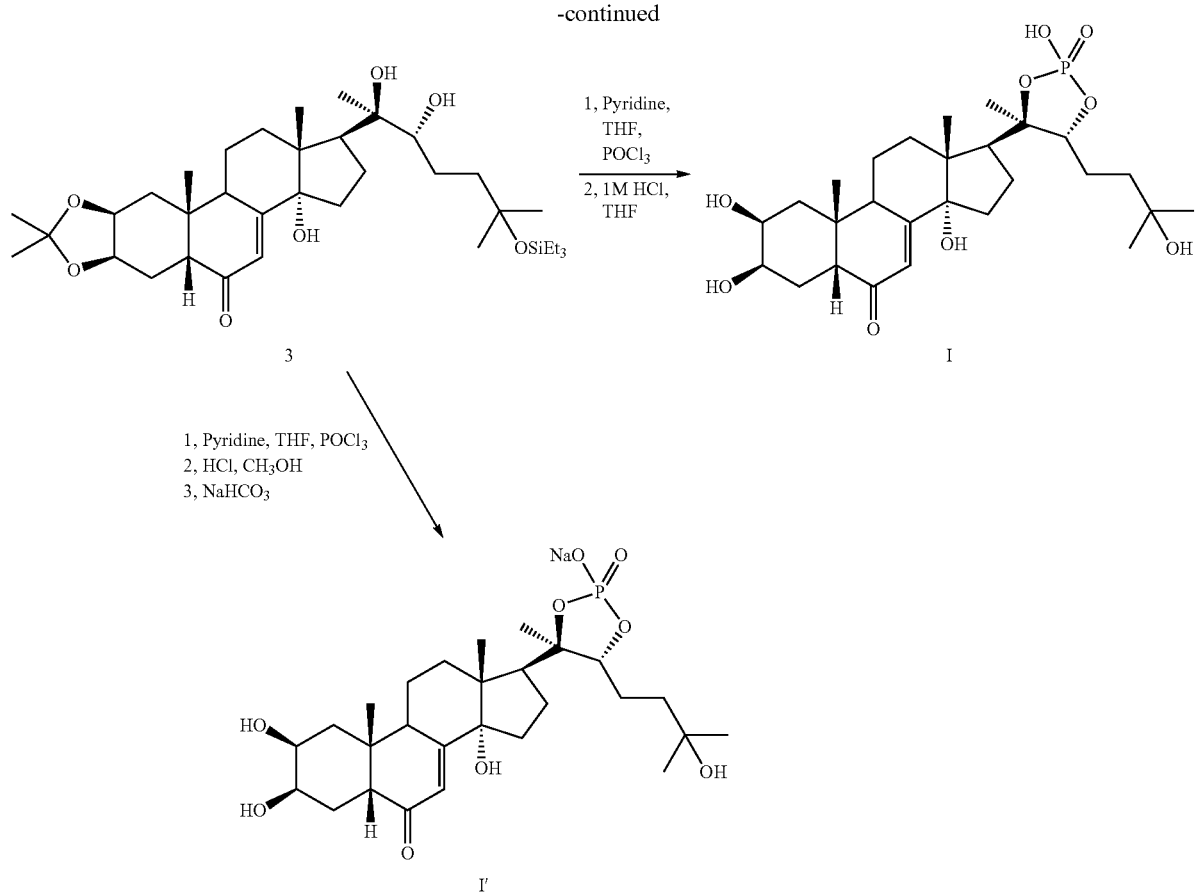

Example 1

Preparation of the Compound of Formula I

Firstly, compound 1 (i.e. the compound of formula IV, wherein $R_1$ and $R_2$ are methyl respectively) was prepared.

20-hydroxy-β-ecdysterone (1.54 g, 3.21 mmol) and phenylboronic acid (412 mg, 3.38 mmol) were dissolved into 20 mL of DMF. The solution was stirred at room temperature for 8 h, and then 40 mL of saturated brine was added. The reaction liquid was diluted with 150 mL of ethyl acetate. The organic layer was washed with saturated brine (50 mL×3), dried over anhydrous sodium sulfate, filtrated, and concentrated to yield white solid. The crude product was directly used to the next step without further purification.

The above crude product and para-toluenesulfonic acid (55 mg, 0.32 mmol) were dissolved into a 40 mL of solvent comprising acetone and 2,2-dimethoxy propane (i.e. formula III, wherein $R_1$, $R_2$, $R_X$ and $R_Y$ are methyl respectively) in a volume ratio of 50:50. The mixture was stirred at room temperature for 12 h, and then 10 mL of $NaHCO_3$ was added to quench the reaction. The organic solvent was evaporated out. The residue was diluted with 150 mL of EtOAc (ethyl acetate), washed with saturated brine (50 mL×3), dried over anhydrous sodium sulfate, filtrated, and concentrated. The residue was separated by column chromatography (50% EtOAc/petroleum) over silica gel, to obtain compound 1 as white foam (1.774 g, 91% yield over two steps).

Secondly, compound 2 (i.e. the compound of formula VI, wherein $R_1$ and $R_2$ are methyl respectively, and $R_3$, $R_4$ and $R_5$ are each independently ethyl) was prepared.

Compound 1 (i.e. the compound of formula IV, wherein $R_1$ and $R_2$ are methyl respectively) prepared above (1.95 g, 3.21 mmol), imidazole (656 mg, 9.63 mmol) and DMAP (4-dimethylaminopyridine, 40 mg, 0.33 mmol) were dissolved into 40 mL of $CH_2Cl_2$. To the solution, TESCl (i.e. the compound of formula V, wherein $R_3$, $R_4$ and $R_5$ are each independently ethyl; X is chlorine) (1.13 mL, 6.43 mmol) was added dropwise at room temperature. The reaction liquid was stirred at room temperature for 4 h, diluted with EtOAc (150 mL), washed with saturated brine (50 mL×3), dried over anhydrous sodium sulfate, filtrated, and concentrated. The residue was separated by column chromatography (17% EtOAc/petroleum) over silica gel, to obtain compound 2 as white foam (2.11 g, yield 91%). $^1$H NMR (400 MHz, $CDCl_3$) δ 7.79 (d, J=7.2 Hz, 2H), 7.46 (t, J=7.2 Hz, 1H), 7.36 (t, J=7.2 Hz, 2H), 5.82 (s, 1H), 4.26-4.21 (m, 2H), 4.13-4.09 (m, 1H), 2.84 (t, J=2.84, 1H), 2.38-2.34 (m, 2H), 2.11-2.04 (m, 3H), 2.04-1.81 (m, 7H), 1.78-1.57 (m, 4H), 1.54-1.45 (m, 1H), 1.50 (s, 3H), 1.34 (s, 3H), 1.33 (s, 3H), 1.27-1.22 (m, 1H), 1.26 (s, 3H), 1.25 (s, 3H), 1.00 (s, 3H), 0.96 (t, J=8.0 Hz, 9H), 0.95 (s, 3H), 0.59 (q, J=8.0 Hz, 6H); $^{13}$C NMR (50 MHz, $CDCl_3$) δ 202.6, 162.9, 134.8, 131.3, 127.9, 127.7, 121.5, 108.3, 86.2, 85.4, 85.0, 73.0, 72.1, 71.6, 51.9, 50.8, 47.3, 42.1, 37.8, 37.6, 34.5, 31.6, 30.9, 30.4, 29.7, 28.5, 26.7, 26.4, 23.6, 22.5, 21.2, 20.5, 17.0, 14.2, 7.1, 6.8; HRMS (M+Na$^+$) calcd for $C_{42}H_{65}BNaO_7Si$ 743.4490. found 743.4452; IR (KBr) 3461, 2959, 1660, 1356, 1242, 1056 cm$^{-1}$.

Thirdly, compound 3 (i.e. the compound of formula VII, wherein $R_1$ and $R_2$ are methyl respectively, and $R_3$, $R_4$ and $R_5$ are each independently ethyl) was prepared.

After dissolving compound 2 prepared above (2.17 g, 3.01 mmol) into 30 mL of $CH_2Cl_2$, 1 M NaOH (20 mL) and 30% $H_2O_2$ (10 mL) were added at room temperature. The reaction liquid was stirred at room temperature for 30 min, and then diluted with EtOAc (100 mL). The organic layer was separated. The organic layer was washed with saturated brine (50 mL×3), dried over anhydrous sodium sulfate, filtrated, and concentrated. The residue was separated by column chromatography (25% EtOAc/petroleum) over silica gel, to obtain compound 3 as white foam (1.88 g, yield 98%). $^1$H NMR (400 MHz, $CDCl_3$) δ 5.82 (d, J=0.8 Hz, 1H), 4.27-4.20 (m, 2H), 3.42 (d, J=10.4 Hz), 2.81 (t, J=8.4 Hz, 1H), 2.36-2.30 (m, 2H), 2.11-2.03 (m, 4H), 1.98-1.93 (dd, J=14.4, 5.6 Hz, 1H), 1.88-1.81 (m, 2H), 1.78-1.66 (m, 6), 1.62-1.46 (m, 2H), 1.48 (s, 3H), 1.37-1.32 (m, 1H), 1.32 (s, 3H), 0.98 (s, 3H), 0.95 (t, J=8.0 Hz, 9H), 0.86 (s, 3H), 0.59 (q, J=8.0 Hz, 6H); $^{13}$C NMR (50 MHz, $CDCl_3$) δ 202.7, 163.3, 121.4, 108.3, 84.9, 76.6, 73.9, 72.2, 71.6, 50.8, 49.1, 47.6, 42.1, 37.8, 37.6, 34.5, 31.8, 31.2, 30.2, 29.7, 28.5, 26.7, 26.4, 26.1, 23.6, 20.8, 20.5, 20.4, 17.4, 7.1, 6.6; HRMS (M+Na$^+$) calcd for $C_{36}H_{62}NaO_7Si$ 657.4163. found 657.4131; IR (KBr) 3450, 2960, 1659, 1378, 1239, 1056 cm$^{-1}$.

Finally, the compound of formula I was prepared.

Compound 3 prepared above (1.28 g, 2.02 mmol) and pyridine (3.4 mL) were dissolved into THF (tetrahydrofuran). $POCl_3$ (0.96 mL, 10.5 mmol) was added dropwise into the reaction liquid under the cooling of ice-water bath. The reaction liquid was stirred at room temperature for 8 h, and then $H_2O$ (2 mL) was carefully added under the cooling of ice-water bath to quench the reaction. The reaction liquid was diluted with EtOAc (150 mL), dried over anhydrous sodium sulfate, filtrated, and concentrated. The crude product was used directly in the next step without further purification.

The crude product as described above was dissolved into 30 mL of THF, and then 1 M HCl (10 mL) was added. The reaction liquid was stirred at room temperature for 12 h, and then concentrated. Residue was separated by C18 column chromatography (20% MeOH/$H_2O$) over silica gel, to obtain the compound of formula I as white powder (880 mg, 80%). $^1$H NMR (400 MHz, $CD_3OD$) δ 5.81 (s, 1H), 4.24 (s, 1H), 3.94 (s, 1H), 3.84-3.81 (m, 1H), 3.16-3.12 (m, 1H), 2.40-2.36 (m, 2H), 2.17-2.10 (m, 2H), 2.02-1.88 (m, 2H), 1.84-1.62 (m, H), 1.54-1.40 (m, 2H), 1.46 (s, 3H), 1.20 (s, 3H), 1.19 (s, 3H), 0.96 (s, 3H), 0.86 (s, 3H); $^{13}$C NMR (50 MHz, $CD_3OD$) δ 206.3, 166.9, 122.4, 91.8, 86.7, 85.0, 70.8, 68.7, 68.5, 51.8, 51.0, 50.9, 41.5, 39.2, 37.4, 35.1, 32.8, 32.1, 31.6, 29.6, 28.9, 25.9, 25.6, 24.4, 22.3, 21.4, 17.4; $^{31}$P NMR δ 15.8 ppm referenced to external $H_3PO_4$; HRMS (M+Na$^+$) calcd for $C_{27}H_{43}NaO_9P$ 565.2542. found 565.2520; IR (KBr) 3412, 2966, 1653, 1384, 1227 cm$^{-1}$.

Example 2

Preparation of Sodium Salt of the Compound of Formula I (i.e. the Compound of Formula I'

Compound 3 prepared in Example 1 (5.00 g, 7.88 mmol) and pyridine (12.7 mL) were dissolved into 50 mL of THF. 5.7 mL of phosphorus oxychloride was added dropwise slowly under the cooling of ice-water bath. After adding, the reaction liquid was reacted at room temperature for 4 h, cooled to −30° C., and then saturated sodium bicarbonate was added dropwise slowly to adjust the pH to 7. The reaction liquid was diluted with EtOAc (150 mL), dried over anhydrous sodium sulfate, filtrated, and concentrated. The crude product was used directly in the next step without further purification.

The above crude product was dissolved into 50 mL of solution (methanol:5% hydrochloric acid=1:9). The reaction liquid was reacted at room temperature for 24 h, and then saturated sodium bicarbonate was added to adjust the pH to 7. The resulting mixture was stirred for 30 min, and filitrated. The filitrate was concentrated under reduced pression at 45° C. After evaporation to dryness, 50 mL of ethanol was added to make the solid dissolve sufficiently, and then filitrated. Then the filitrate was concentrated under reduced pression at 45° C. After evaporation to dryness, by column chromatography (elute:dichloromethane:methanol=3:1), sodium salt of the compound of formula I as white powder (2.5 g, 56%) was obtained. $^1$H NMR (400 MHz, $CD_3OD$) δ 5.80 (s, 1H), 4.13 (dd, J=9.2, 2.8, 1H), 3.95 (s, 1H), 3.84-3.81 (m, 1H), 3.17-3.13 (m, 1H), 2.40-2.33 (m, 2H), 2.20-2.11 (m, 2H), 1.99-1.58 (m, 12H), 1.51-1.40 (m, 2H), 1.42 (s, 3H), 1.20 (s, 3H), 1.18 (s, 3H), 0.96 (s, 3H), 0.86 (s, 3H); $^{13}$C NMR (50 MHz, $CD_3OD$) δ 206.3, 167.3, 122.2, 88.8, 85.1, 84.6, 70.9, 68.6, 68.4, 51.7, 50.9, 50.8, 42.0, 39.2, 37.3, 35.0, 32.8, 32.1, 31.7, 29.7, 28.8, 25.9, 25.8, 24.5, 22.4, 21.5, 17.5; $^{31}$P NMR δ 14.3 ppm referenced to external $H_3PO_4$; HRMS (M+H$^+$) calcd for $C_{27}H_{43}NaO_9P$ 565.2542. found 565.2540; IR (KBr) 3406, 2966, 1651, 1382, 1206 cm$^{-1}$.

Example 3

Preparation of a Pharmaceutical Composition Tablet Comprising 5 mg of the Compound of Formula I The pharmaceutical composition tablet comprises the following components:

| | |
|---|---|
| the compound of formula I | 5 mg |
| lactose | 70 mg |
| microcrystalline cellulose | 40 mg |
| hypromellose | 2 mg |
| lower substituted hydroxypropylcellose | 10 mg |
| magnesium stearate | 1 mg |

The pharmaceutical composition tablet was prepared via the following steps from each component of the content as described above:

The hypromellose was dissolved by a suitable amount of water, which is ready for use;

the active ingredient (the compound of formula I) and lactose, microcrystalline cellulose, lower substituted hydroxypropylcellose were mixed uniformly; a suitable amount of hypromellose solution was added, and then the resulting mixture was stirred to prepare softmaterial;

the softmaterial was granulated via a 20-mesh sieve, to obtain wet granules;

the wet granules were dried at 40~50, to obtain dry granules;

the dry granules were passed through a 20-mesh sieve to finish;

magnesium stearate was added, and mixed uniformly;

the content of granules was determined, and the weight of tablet was calculated, and then tabletting.

Example 4

Preparation of a Pharmaceutical Composition Tablet Comprising 100 mg of the Compound of Formula I The pharmaceutical composition tablet comprises the following components:

|  |  |
| --- | --- |
| the compound of formula I | 100 mg |
| lactose | 150 mg |
| microcrystalline cellulose | 100 mg |
| hypromellose | 4 mg |
| lower substituted hydroxypropylcellose | 20 mg |
| magnesium stearate | 4 mg |

The pharmaceutical composition tablet was prepared via the following steps from each component of the content as described above:

The hypromellose was dissolved by a suitable amount of water, which is ready for use;

the active ingredient (the compound of formula I) and lactose, microcrystalline cellulose, lower substituted hydroxypropylcellose were mixed uniformly; a suitable amount of hypromellose solution was added, and then the resulting mixture was stirred to prepare softmaterial;

the softmaterial was granulated via a 20-mesh sieve to obtain wet granules;

the wet granules were dried at 40~50° C., to obtain dry granular;

the dry granules were passed through a 20-mesh sieve to finish;

magnesium stearate was added, and mixed uniformly;

the content of granules was determined, and the weight of tablet was calculated, and then tabletting.

Example 5

Preparation of Pharmaceutical Composition Capsule Comprising 50 mg of the Compound of Formula I The pharmaceutical composition capsule comprises the following components:

|  |  |
| --- | --- |
| the compound of formula I | 50 mg |
| lactose | 50 mg |
| Micro powder silica gel | 3 mg |
| magnesium stearate | 1 mg |

The pharmaceutical composition capsule was prepared via the following steps from each component of the content as described above:

the active ingredient (the compound of formula I), lactose, micro powder silica gel, and magnesium stearate were mixed uniformly; the content of powder was determined, the load was calculated, and then the mixture was loaded into a hard capsule with a suitable size.

Experiment Example 1

The Experiment for In Vitro Glucose Consumption in HepG2 Cells of the Compound of Formula I The experiment for in vitro glucose consumption in HepG2 cells was performed on the compound of formula I prepared in Example 1, as follows:

HepG2 cells with good growth state were selected, and were digested with trypsinase and EDTA (ethylene diamine tetraacetic acid) digestive juice. After digestion was complete, the resulting mixture was formulated with DMEM (Dulbecco's Modified Eagle Medium) having 10% Fetal bovine serum (FBS) into single cell suspension. The cells were seeded into 96 well plates, with $1*10^4$ cells per well. Once the cell confluence reached 50%, the medium was changed to high glucose DMEM without serum, starvation cultured for 12 h. The cell supernatant was pipetted, and fresh high glucose DMEM with or without medications was added. The cells were divided into a blank control group, a 20-hydroxy-β-ecdysterone group, and a compound of formula I group. After culturing for 24 h, each group was tested for the change of glucose in the medium by using the glucose oxidase method. The test result was shown in table 1 below.

TABLE 1

The effects of the compound of formula I and 20-hydroxy-β-ecdysterone on glucose consumption in HepG2 cells ($\bar{x} \pm s$, n = 8)

| Group | Concentration of the medication (M) | Glucose consumption (mM) | Glucose consumption increased (mM) |
| --- | --- | --- | --- |
| blank control group |  | 1.32 ± 0.17 | — |
| 20-hydroxy-β-ecdysterone | $2 \times 10^{-7}$ | 1.45 ± 0.28 | 0.13 |
|  | $2 \times 10^{-8}$ | 1.38 ± 0.11 | 0.06 |
|  | $2 \times 10^{-9}$ | 1.30 ± 0.23 | — |
| the compound of formula I | $2 \times 10^{-7}$ | 6.96 ± 0.23 | 5.64 |
|  | $2 \times 10^{-8}$ | 6.51 ± 0.12 | 5.19 |
|  | $2 \times 10^{-9}$ | 6.46 ± 0.19 | 5.14 |

The experimental results are shown in table 1. The compound of formula I possesses significant activity in lowering glucose, and in a concentration range of $2\times10^{-7}$~$2\times10^{-9}$ M could increase the glucose consumption in HepG2 cells by above 500%. Whereas 20-hydroxy-β-ecdysterone in concentration of $2\times10^{-7}$~$2\times10^{-8}$ M increases the glucose consumption in HepG2 cells by below 15%, and when the concentration is diluted into $2\times10^{-9}$ M, 20-hydroxy-β-ecdysterone has no effect for lowering glucose in HepG2 cells. Therefore, when compared with the activity in lowering glucose of parent compound 20-hydroxy-β-ecdysterone, the activity in lowering glucose of the compound of formula I is significantly superior to that of 20-hydroxy-β-ecdysterone.

Experiment Example 2

The Dissolution Experiment for the Compound of Formula I and the Sodium Salt Thereof The compound of formula I (prepared according to the method in Example 1) is white or off-white crystal powder, with the melting point being 164~477° C., the molecular formula being $C_{27}H_{43}O_9P$, and the molecular weight being 542.6. The amount of water necessarily for completely dissolving this product (1 g) is 12 mL. The solubility of this product is 10 fold of that of 20-hydroxy-β-ecdysterone.

The sodium salt of the compound of formula I (prepared according to the method in Example 2) is white or off-white crystal powder, with the melting point being 173~185° C., the molecular formula being $C_{27}H_{42}O_9NaP$, and the molecular weight being 564.6. The amount of water necessarily for completely dissolving this product (1 g) is 2.5 mL. The solubility of this product is 50 fold of that of 20-hydroxy-β-ecdysterone.

Experiment Example 3

The Pharmacological Experiment for the Compound of Formula I and the Sodium Salt Thereof The pharmacological experiments were performed on the compound of formula I and the sodium salt thereof prepared in Example 1 and Example 2 as follows:

40 male mice with a body weight of 21±1.8 g (Kunming mouse: SPF grade, male, provided by laboratory animal centre of Sichuan Academy of Chinese Medicine Sciences) were grouped into 4 groups randomly, which are control group, 5 mg/kg of the compound of formula I group, 5 mg/kg of the sodium salt of the compound of formula I group, and 25 mg/kg of Glibenclamide (manufactured by Tianjin Pacific Chemical & Pharmaceutical Co., LTD) group. For the control group, distilled water was given, while for other groups, corresponding medicaments were given. The medicament was intragastrically administered in 0.2 ml/10 g of administration volume twice daily. The administration was continued for 19 times. On the $5^{th}$ time and $19^{th}$ time and after thoroughly fasting for 2 h, the blood glucose value for each mouse was tested by a Blood Glucose Meter, and the results were recorded as follows:

TABLE 2

The effects of the compound of formula I and the sodium salt thereof on the level of blood glucose in normal mice ($\overline{X} \pm S$)

| Group | Dose (mg/kg) | The number of animals | Blood glucose mmol/L | |
| --- | --- | --- | --- | --- |
| | | | 3 d after dosing | 10 d after dosing |
| control | | 10 | 11.4 ± 2.1 | 11.5 ± 1.9 |
| the compound of formula I | 5 | 10 | 10.4 ± 1.7 | 9.1 ± 2.3* |
| sodium salt of the compound of formula I | 5 | 10 | 10.2 ± 1.9 | 9.8 ± 1.4* |
| Glibenclamide | 25 | 10 | 9.3 ± 0.9* | 9.9 ± 0.9* |

Compared with control group: *P<0.05.

Based on table 2, the compound of formula I and the sodium salt thereof have the effects in lowering glucose in normal mice.

INDUSTRIAL APPLICABILITY

The invention prepares a novel compound with a stable structure, good solubility in water, and excellent activity in lowering glucose.

What we claim is:

1. A compound of the structure of formula I:

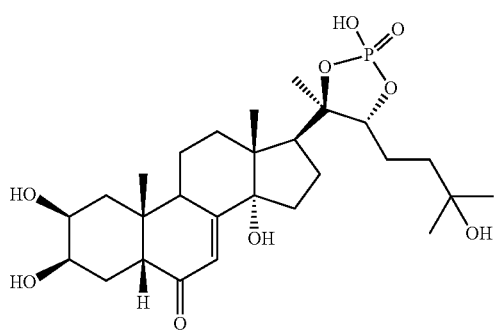

or pharmaceutically acceptable salts thereof.

2. The compound of claim 1, wherein the pharmaceutically acceptable salts are selected from metal salts, or organic amine or ammonium salts.

3. The compound of claim 2, wherein the metal salts are sodium salt, wherein the compound is of formula I':

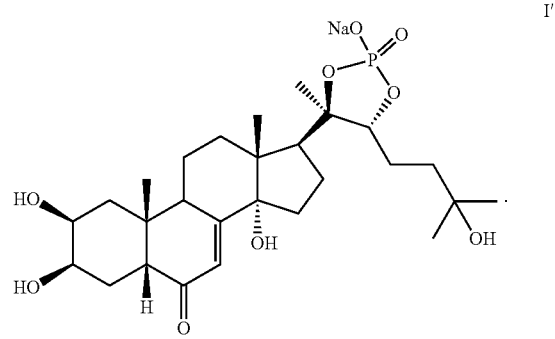

4. A method for preparing the compound of claim 1, comprising the steps of:

(1) using 20-hydroxy-β-ecdysterone as a starting material to react with phenylboronic acid in the presence of an organic solvent, to yield a compound of formula II:

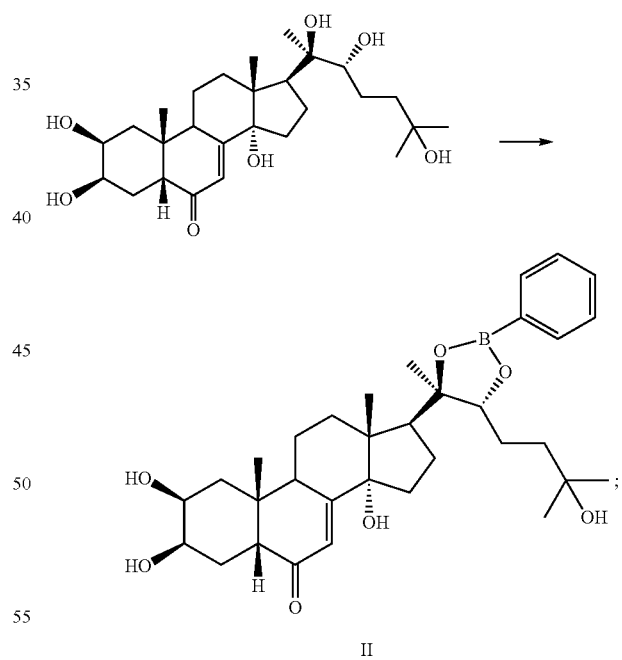

(2) reacting the compound of formula II with a compound of formula III under acidic condition to yield a compound of formula IV; wherein, $R_1$ and $R_2$ in the compounds of formulas III and IV are each independently hydrogen, C1-C4 alkyl or phenyl, $R_X$ and $R_Y$ are each independently C1-C4 alkyl, phenyl, or $R_X O—$ and $R_Y O—$, together with the carbon to which they are attached, form carbonyl:

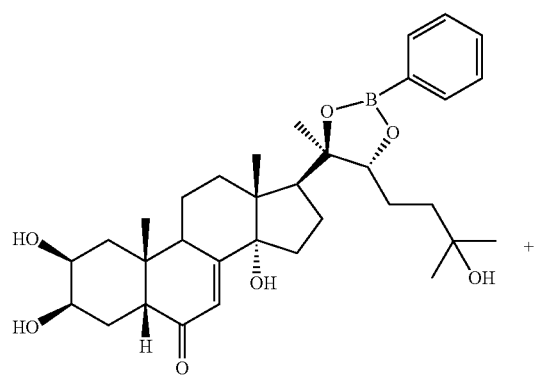

II

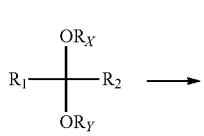

III

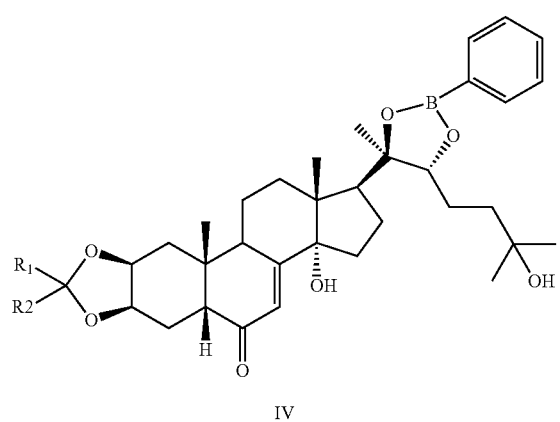

IV (3) reacting the compound of formula IV with a compound of formula V, to yield a compound of formula VI, wherein $R_3$, $R_4$ and $R_5$ in formula V are each independently selected from C1-C4 alkyl; X is halogen; the definitions of $R_1$, $R_2$, $R_3$, $R_4$ and $R_5$ in formula VI are the same as those in formula IV and formula V:

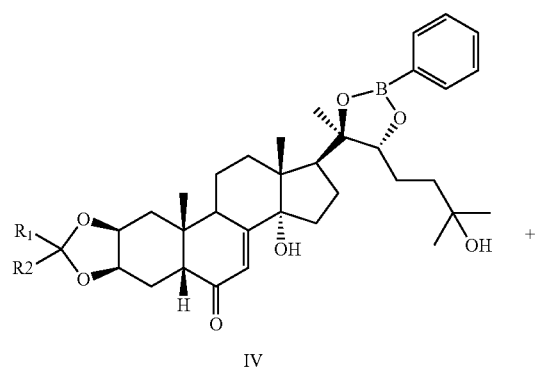

IV

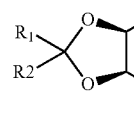

V

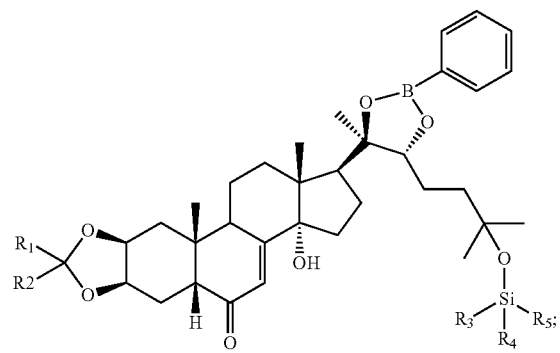

VI (4) deprotecting the compound of formula VI in the presence of a base and a peroxide, to yield a compound of formula VII; the definitions of $R_1$, $R_2$, $R_3$, $R_4$ and $R_5$ in formula VII being the same as those in formula IV and formula V:

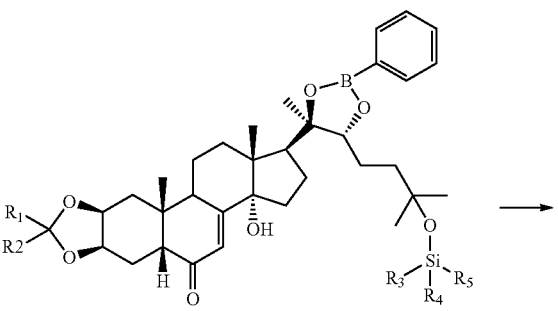

VI

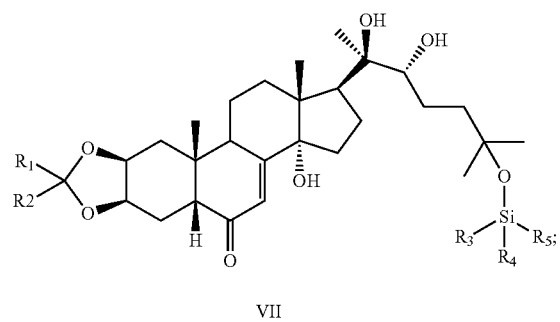

VII (5) reacting the compound of formula VII with $POCl_3$, to yield a compound of formula VIII, the definitions of $R_1$, $R_2$, $R_3$, $R_4$ and $R_5$ in formula VIII being the same as those in formula IV and formula V:

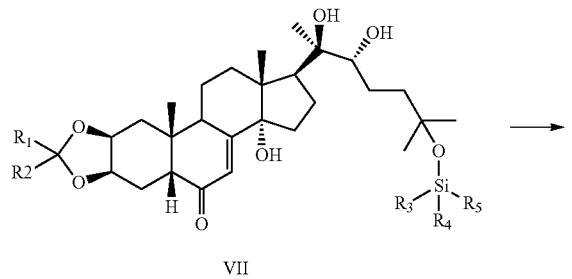

VII

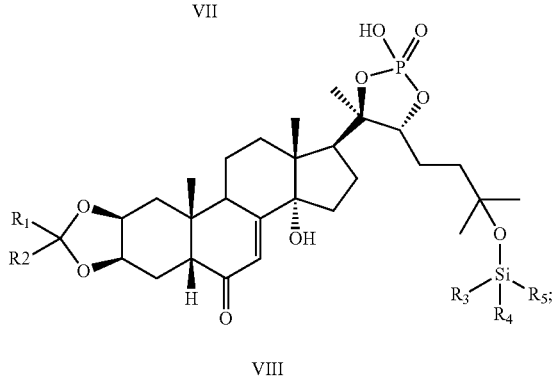

VIII (6) deprotecting the compound of formula VIII under acidic condition, to yield the compound of formula I:

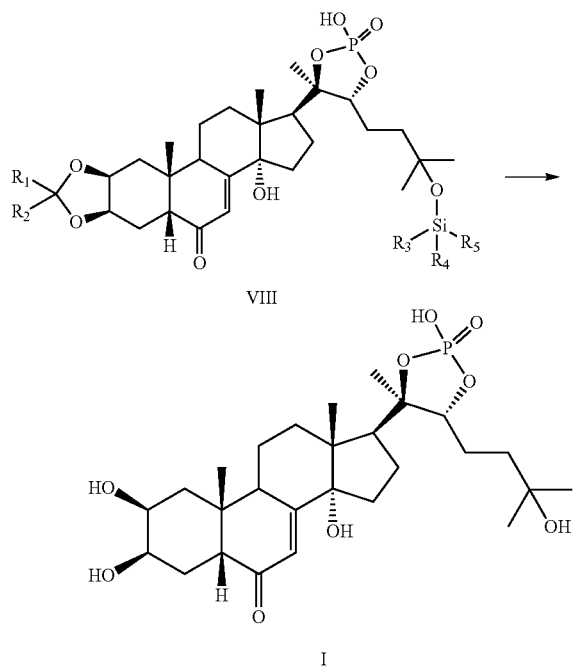

VIII

I

5. The method of claim 4, after obtaining the compound of formula I in step (6), a conventional salification method is used to yield the salt of the compound of formula I.

6. The method of claim 4, wherein $R_1$, $R_2$, $R_X$ and $R_Y$ in the compound of formula III in step (2) are simultaneously methyl.

7. The method of claim 4, wherein $R_3$, $R_4$ and $R_5$ in the compound of formula V in step (3) are simultaneously methyl or ethyl; X is chlorine.

8. The method of claim 4, wherein the organic solvent in the step (1) is selected from dimethylformamide, dimethylacetamide, tetrahydrofuran or dimethyl sulfoxide; the reaction temperature is 0~50° C.;

the acidic condition in the step (2) means in the presence of an acidic catalyst, and the acidic catalyst is selected from para-toluenesulfonic acid, pyridinium para-toluenesulfonate, or stannous chloride;

the reaction in the step (3) is carried out in the presence of an organic base and an activator; the organic base is selected from imidazole, N-methylmorpholine, pyridine, or triethylamine, the activator is selected from 4-dimethylaminopyridine, or dimethylformamide;

the base in the step (4) is sodium hydroxide, potassium hydroxide, potassium carbonate, or sodium carbonate, and the peroxide is hydrogen peroxide;

the reaction in the step (5) is carried out in the presence of an organic base, and the organic base is selected from pyridine, triethylamine, or imidazole.

9. A pharmaceutical composition comprising the compound of claim 1.

10. A method for lowering glucose comprising administering an effective amount of the compound of claim 1 to a subject in need thereof.

11. A pharmaceutical composition comprising the compound of claim 2.

12. A pharmaceutical composition comprising the compound of claim 3.

13. A method for lowering glucose comprising administering an effective amount of the compound of claim 2 to a subject in need thereof.

14. A method for lowering glucose comprising administering an effective amount of the compound of claim 3 to a subject in need thereof.

* * * * *